United States Patent [19]

Dickinson, III et al.

[11] 4,091,807

[45] May 30, 1978

[54] INTRA-VAGINAL DEVICE AND METHOD OF USE

[76] Inventors: Ben Wade Oakes Dickinson, III, 2125 Broderick St., San Francisco, Calif. 94115; Robert Wayne Dickinson, 40 Maplewood Dr., San Rafael, Calif. 94901

[21] Appl. No.: 738,886

[22] Filed: Nov. 4, 1976

[51] Int. Cl.² ............................................... A61F 5/46
[52] U.S. Cl. ................................................... 128/130
[58] Field of Search ............................... 128/127–131, 128/260, 341, 343

[56] References Cited

U.S. PATENT DOCUMENTS

| | | | |
|---|---|---|---|
| 3,757,775 | 9/1973 | Marco et al. | 128/130 |
| 3,811,423 | 5/1974 | Dickinson et al. | 128/343 X |
| 3,994,291 | 11/1976 | Salmasian | 128/130 |

*Primary Examiner*—Lawrence W. Trapp
*Attorney, Agent, or Firm*—Flehr, Hohbach, Test, Albritton & Herbert

[57] ABSTRACT

A device is inserted into the vagina of a female animal, such as of the bovine, porcine, ovine, equine, or caprine species. Long-term retention enhances the quality and quantity of meat produced by the animal. In one embodiment, the device includes a central shaft which carries two axially spaced mounting rings to which are affixed a plurality of elongate resilient rods which radiate to terminate in free ends of enlarged bulbous configuration. The device is inserted into the animal's vagina with a speculum. The bulbous ends of the rods are urged to engage and become embedded in the animal's vaginal lining for long-term retention.

12 Claims, 7 Drawing Figures

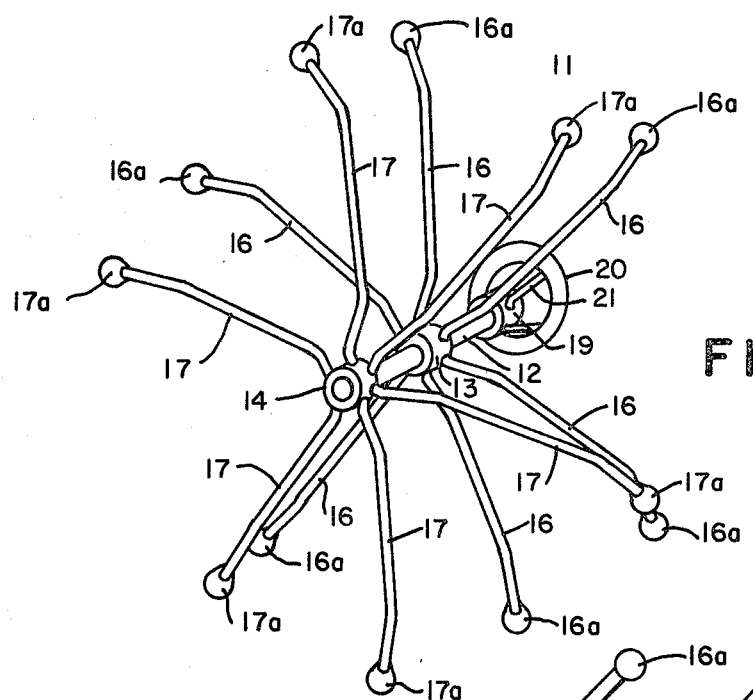
FIG.—1
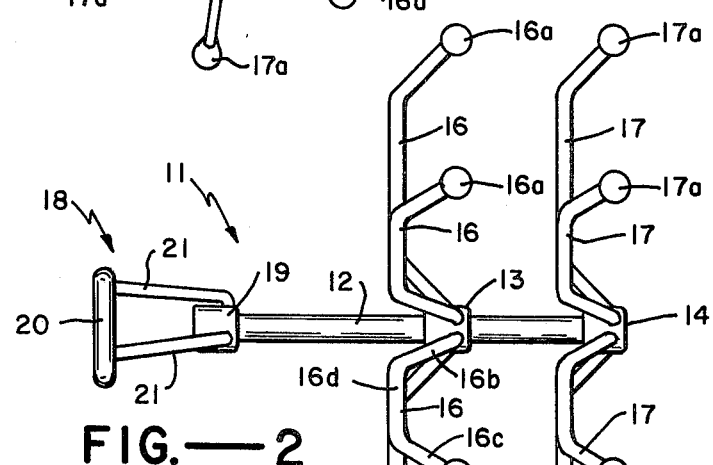
FIG.—2
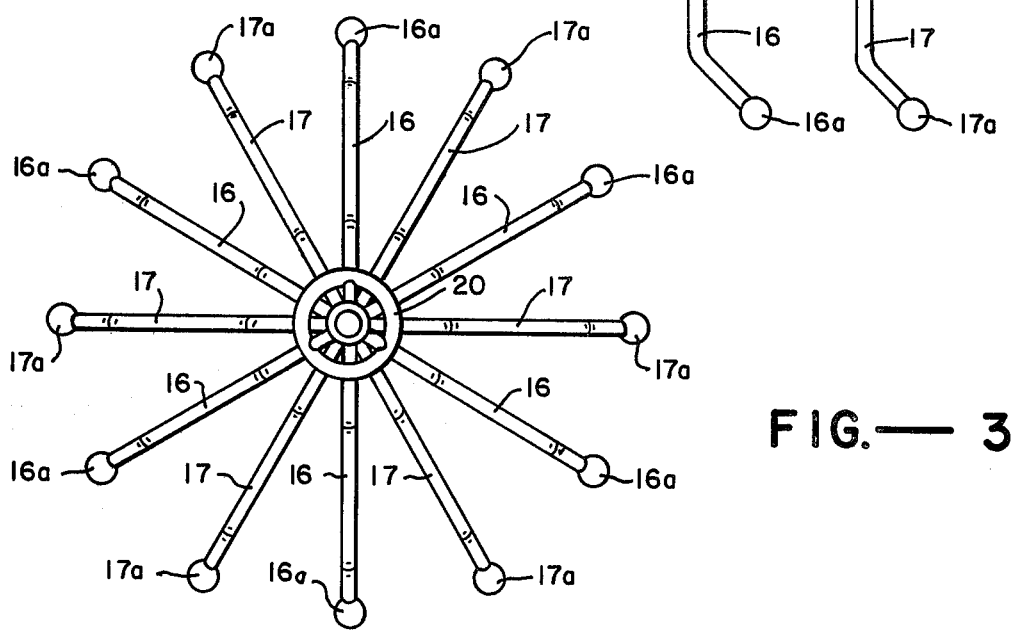
FIG.—3

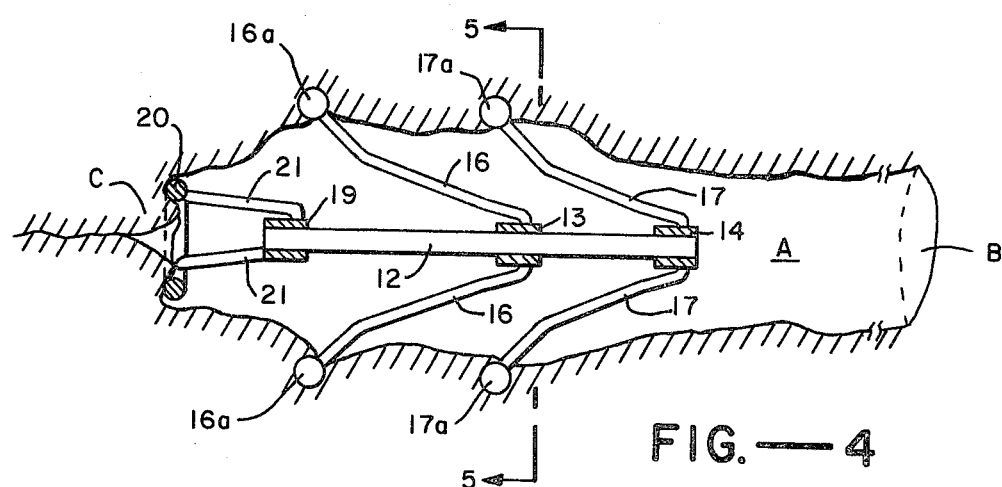
FIG.—4
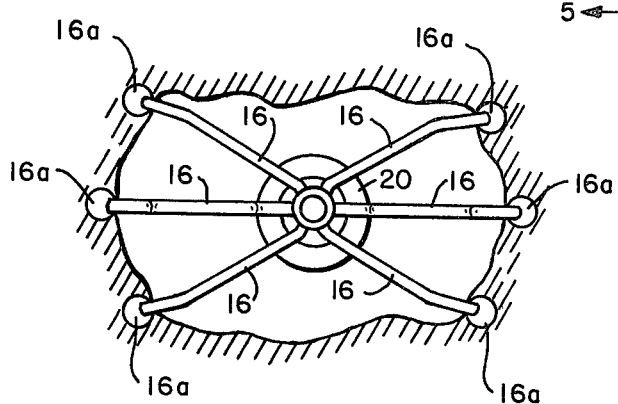
FIG.—5
FIG.—6
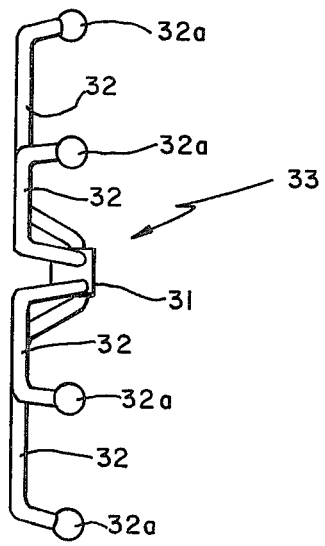
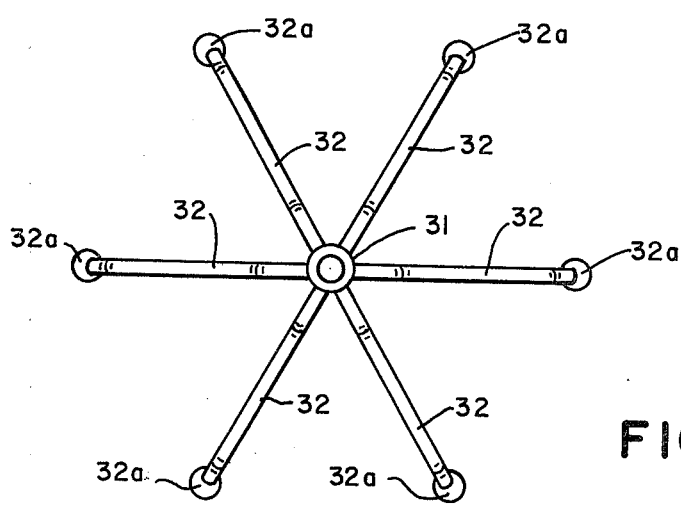
FIG.—7

INTRA-VAGINAL DEVICE AND METHOD OF USE

BACKGROUND OF THE INVENTION

A number of intra-vaginal devices have been described in our U.S. Pat. No. 3,811,423. Such devices function as anchor assemblies including a number of spring-like strands each in a hoop configuration mounted at opposite ends to mounting rings. Such devices may include a cervical clamping ring. Other similar devices are described in British Pat. No. 1,384,254. Such devices are constructed to prevent simultaneous expulsion thereof by the animal. Although the devices are highly effective for retention in the vaginal lumens of animals such as pigs and cows post-parturition when the vaginal linings of such animals have been distended, they are not as effective for retention in pre-parturition animals.

Many intra-uterine devices have been developed for the purpose of contraception. However, retention of such devices in the uterus is substantially less difficult than retention in the vagina. Retention in the uterus is facilitated by the cervix, located at the uterus entrance, a tightly closed passageway which effectively blocks expulsion of the device. In contrast, the vaginal lining of an animal such as the cow includes a sphincter-like muscle. However, it does not provide a normally tightly closed constriction such as the cervix. Also, the animal's vagina tends to eject foreign bodies. Because of such distinctions, devices retained for long periods of time in the uterus may not be effective for retention in the vagina.

One intra-uterine contraception device is set forth in British Pat. No. 1,129,712. In the embodiment of FIGS. 1-5, a number of thin filaments (cross-section of 1.5 mm) project from an elliptical loop. These soft, pliable, thin filaments have little structural strength. The patent states at page 2, lines 98-103, that rounded corners at the filament ends which could constitute projections should be avoided. There is no suggestion that such a device be adaptable for retention in an animal's vagina. Assuming there were such a suggestion, a device of the indicated type would not be effective for that purpose.

SUMMARY OF THE INVENTION AND OBJECTS

The present invention relates to a method and device for enhancing the quality and quantity of meat produced by female animals, such as of the bovine, porcine, ovine, equine, or caprine species. The device is placed into the animal's vagina and retained therein over a prolonged period of time.

The device of the present invention includes mounting means comprising at least one ring from which a plurality of elongated resilient strands project radially ourwardly terminating in free ends of enlarged bulbous configuration. The device is inserted into the vagina, as in a speculum, with the bulbous ends directed toward the anterior of the vagina. Preferably, the device includes a number of offset angle bends to provide a spring-like pressure to the bulbous ends so that, in position, they become embedded in the animal's vaginal lining without piercing it. After a period of time, the vaginal lining grows partially or fully over the bulbous ends to form bonds to assist in retention. The rods are preferably formed of a material, such as nylon, which becomes more flexible during vaginal retention to cause a decrease in the outward pressure exerted by the bulbous ends to reduce irritation. A preferable device includes two rings of the foregoing type spaced on a central shaft which serves to align the device in the animal's vagina.

For use in a cow or other animal whose vagina includes a projecting cervix, a cervical ring is mounted to the leading edge of the shaft to contact the cervix and assist in retention of the device and to proclude inadvertent penetration of the vaginal wall during insertion.

It is an object of the invention to provide a device capable of long-term retention in an animal's vagina without harmful side effects to the animal to promote weight gain of the animal.

Further objects and features of the present invention will be apparent from the following description taken in conjunction with the accompanying drawing.

BRIEF DESCRIPTION OF THE DRAWINGS

FIG. 1 is a perspective view of a preferred embodiment of the device of the present invention.

FIGS. 2 and 3 are side elevational and end views, respectively, of the device of FIG. 1.

FIG. 4 is a cross-sectional view of the device of FIG. 1 retained in the vagina of a cow.

FIG. 5 is a cross-sectional view taken along the line 5—5 of FIG. 4.

FIGS. 6 and 7 are side elevational and end views, respectively, of another embodiment of the present invention particularly adapted for use in a pig.

DETAILED DESCRIPTION OF THE PREFERRED EMBODIMENTS

The device of the present invention serves to enhance the quality and quantity of meat produced by animals of the bovine, porcine, ovine, equine, or caprine (goat) species. As set forth below, the device is inserted into the vagina of the animal between its vulva and cervix and retained therein. It has been found that such retention promotes weight gain of the animal.

Referring to FIG. 1, the illustrated device is particularly adapted to retention in the vagina of the cow for promoting weight gain. In the illustrated embodiment, such device 11 includes an elongate shaft 12 to which is firmly affixed mounting means comprising axially spaced annular mounting rings 13 and 14. Mounting ring 14 is disposed at the trailing edge of device 11 as it is inserted into the animal's vagina.

A plurality of elongate resilient rods 16 are rigidly mounted at their fixed ends to mounting ring 13. In the illustrated embodiment, six rods 16 are mounted in equidistant, spaced-apart configuration to radiate outwardly in star-like or spider-like composite configuration. Rods 16 terminate at their free ends in large bulbous or ball-like shapes 16a to be described in more detail hereinafter. It should be recognized that more or fewer rods may be used in certain instances.

Referring to FIGS. 1-3, rods 16 in a non-compressed or free state project from mounting ring 13 at a substantial angle to the central axis of shaft 12, at 45° in the illustrated embodiment. Such rods also include at least two distinct off-set angle bends in a generally outward direction from the mounting ring 13 as clearly illustrated in FIG. 2. Such bends define an inner rod segment 16b mounted to ring 13, an outer rod segment 16c terminating in end 16a and at least one middle rod segment 16d defined at its ends by bends in the rods.

By forming outer rod segment 16c substantially shorter than the total length of the middle and inner rod segments, the pressure exerted on the bulbous end is increased when subjected to a bending moment toward the mounting means.

In the illustrated embodiment, the bend between segments 16b and 16d is approximately 135° and the bend between segments 16c and 16d is approximately at the same angle.

Six equidistant spaced rods 17 project from mounting ring 14 to terminate at their free ends 17a in enlarged bulbous configurations similar to 16a. In general, rods 17 are of the same type as rods 16 and so the description with respect to rods 16 will also apply to rods 17. The purpose of employing two spaced mounting rings for supporting spaced sets of rods is to provide a sufficient number of bulbous ends to anchor the device to prevent spontaneous ejection. By spacing two sets of the bulbous ends axially from each other, the outer radial extent of the device, as in a speculum, can be limited to one-half the same extent which would be possible if all twelve bulbous ends were mounted to the same mounting ring. To further assist in nesting of rods 16 and 17 upon compression into a speculum, the two sets of rods are circumferentially off-set as illustrated in FIG. 3. In animals characterized by a tight vulva and/or vaginal sphincter muscle, it is particularly advantageous for the device to be able to be compressed to a small radial extent.

Referring again to FIGS. 1–3, an annular cervical seating means is mounted to the leading end of shaft 12 which is adapted for encircling an animal's projecting cervix as of a cow to assist retention. Such seating means, generally designated by the number 18, includes a mounting ring 19 carried by shaft 12, interconnected to an annular cervical ring 20 by arms 21. For use with an animal having a cervix projecting into the vagina, cervical seating means 18 serves not only to mate with the vagina to assist retention but also as a positioning point for the device.

Rods 16 are characterized by a combination of internal memory and a configuration of changing axial direction, such as the multiple bends set forth above, so that when the rods are subjected to a bending moment to move bulbous ends 16a toward each other, such ends resist and are urged under spring-like pressure in a radially outward direction from the mounting rings. Also, the rods of the present invention should be capable of performing the following specific objectives: (1) ready compression into a speculum small enough to be inserted past the animal's vulve and sphincter muscle into the anterior portion of the vaginal lumen; (2) sufficient rigidity to permit bulbous ends 16a to become embedded into the animal's vaginal lining for sufficient time for the vaginal lining to grow over the bulbous ends and to form a bond therewith or envelopment thereof; and (3) the ability to become more flexible or flaccid during vaginal retention to cause a decrease in the outward pressure exerted by the bulbous ends during the retention period.

The above objectives are accomplished with a combination of a suitable biologically compatible material for constructing the rods and ends, and a suitable dimension for each rod and the enlarged bulbous ends thereof. It has been found that a particularly effective material for this purpose is a standard nylon such as formed of a homopolymer sold under the trademark "Kapron" by Allied Chemical Corporation. Such nylon is hygroscopic and tends to become more flexible under the humid conditions within the vagina and at the warm temperature of the animal's vagina during retention.

It has been found that when rods 16 are formed of a material such as the foregoing nylon type, a suitable diameter of the rod is from about 1 to 4 mm., and preferably about 2.5 mm.

The presence of bulbous ends 16a is an important feature of the present invention. It has been found that if the bulbous ends are too small they tend to penetrate and pierce the vaginal wall to cause damage to the animal. On the other hand, if the bulbous ends are too large, the effective retention of the of the device is decreased because the tissue will not attach to or envelop the ends. Suitable sizes for such enlarged ends is greater than 3 mm but less than 10 mm, and preferably about 6 mm in diameter. Such bulbous ends need not be perfectly spherical so long as they are sufficiently rounded to prevent damage to the vaginal wall. It is noted that the foregoing limitations of suitable rods and bulbous ends indicates that said ends should be enlarged in comparison to the remainder of the rods as illustrated in the drawings.

Suitable dimensions for the foregoing device are as follows: total length of rods (16 and 17): 8 cm; length of shaft (12): 10 cm; diameter of rings (13 and 14): 1 cm.

A device of the foregoing type is inserted into an animal's vagina as follows. Firstly, pressure is applied to rods 16 and 17 to move bulbous ends 16a and 17a, respectively, toward each other to thereby reduce the outward radial extent of the same. A particularly effective way to accomplish this is to insert the entire device into a speculum or hollow tube, the trailing edge first. Then, the speculum is inserted through the animal's vulva into its vagina with the bulbous ends thereof directed toward the anterior of the animal's vagina.

When the device assumes its position adjacent the animal's cervix at the anterior end of the vagina, the speculum is removed to leave the device in place. This is suitably accomplished by pushing a rod in through the speculum from the external end thereof to contact the device and force it out of the speculum or by pulling the speculum out of the vagina and holding the inner rod stationary.

After release from the speculum, rods 16 and 17 expand outwardly under sufficient pressure that bulbous ends 16a and 17a become embedded in the animal's vaginal lining but without piercing the same. The device does not prevent the vulva from assuming its normally closed position. Referring to FIG. 4, the animal's vaginal lumen is illustrated by the letter "A", its vulva at the posterior end by the letter "B", and its cervix at the anterior end by the letter "C". It is noted that the normal position of a cow's vagina is relatively flat and is characterized by many folds in the vaginal lining. When the device is inserted, it expands the vaginal lumen as illustrated in FIGS. 4 and 5.

As set forth above, rods 16 and 17 are most rigid during the beginning of retention, say up to 10 days. During this time, it is believed that such rod rigidity is the primary mode of retention. During this time, it has been found that the vaginal lining of the animal grows over the bulbous ends thereof to form a bond therewith. Meanwhile, the rods become more flexible to decrease the outward pressure exerted by the bulbous ends during the retention period. It is believed that at some time subsequent to the first 10 days of retention, the bond formed between the vaginal lining and bulbous ends becomes a major factor in retention of the device. During this time, potential irritation to the animal is decreased due to the greater flexibility of the rods.

Controlled testing has been performed to illustrate that when devices of the foregoing type are placed in heifers, the quality and quantity of meat produced by the animal is enhanced in comparison to ones without devices. Such enhancement is defined herein to include one or more of the following effects:

(1) improvement in the rate of gain in weight (average daily gain);
(2) improvement in the feed efficiency (reduction in conversion ratio in pounds of feed consumed per pound of grain);
(3) improvement in the quality of the meat (a better distribution of the fat in the tissue (marbling) according to U.S.D.A. meat grading standards); and
(4) improvement in carcass yield (higher proportion of slaughtered and eviscerated carcass weight to live animal weight).

For example, one series of tests performed at the University of California at Davis show that the deviced animals as compared to the undeviced control ones, showed an overall average of 6% greater aveage daily weight gain, with 12% greater average daily weight gain demonstrated in the younger animals.

It has been found that device retention in the pre-parturition heifers is more difficult with various devices than is device retention in post-parturition animals such as cows. This is because the vaginas of the latter type of animals is relatively flaccid and more readily retains such devices. It has further been found that devices of the foregoing type are retained in almost 100% of such pre-parturition animals.

Referring to Figs. 6 and 7, another embodiment of the present invention is illustrated which is particularly adapted for use in the pig. Such device, generally designated by the number 30, includes mounting means comprising annular mounting ring 31, and six rods 32 and 32a. The device includes only a single ring and set of radiating rods in composite forming a star-shaped or spider-shaped configuration. Also, rods 32 are shorter than rods 16 and 17 to accomodate the differences in sizes between the vaginas of the pig in comparison to that of the heifers in which the device of FIGS. 1–3 is inserted. Another difference is that no central shaft is included to axially align the device. The rods of the two devices are similar including multiple bends serving the same purposes. Thus, the foregoing description with respect to such rods in FIGS. 1–3 applies to the rods of FIGS. 6 and 7.

A device of the type illustrated in FIGS. 6 and 7 is inserted into the animal's vagina in a speculum of the foregoing type. During compression for insertion into the speculum for insertion, the bulbous ends 32a urged toward each other to form the leading edge of the device on insertion into the speculum. In other words, mounting ring 31 first is inserted into the speculum and rods 32 are then nested therein. A smaller speculum is employed for passage through the smaller vulva of the pig in comparison to the heifer.

One of the advantages of the device of FIGS. 6 and 7 is that it is relatively inexpensive to construct and fits into the smaller vaginal lumen of the pig in comparison to the heifer. On the other hand, the degree of retention is not as great as that of the devices of FIGS. 1–3. The former device may be employed in a smaller version without cervical seating means 18 for use in the vagina of the porcine species (e.g., pig) to enhance the quality and quantity of meat produced by the animal.

It has been found that isolation of the deviced female animals from intact or neutered male animals of the same species improves the performance of the device enhancing the quality and quantity of meat production as defined herein. It is believed that this effect is due to the elimination of heterosexual stimulation.

The device may be used alone or in consort with certain exogeneous chemicals such as (a) ones containing or stimulating estrogen (e.g., sold under the name Synovex-H or diethyl stibesterol), (b) recorcyclic acid lactones (e.g., Ralgro), or (c) rumen volatile fatty acid affectors (such as sold under the name Rumensin). These chemicals also improve the performance of the devices. Conventionally, the chemicals are subcutaneously implanted in the ear of the animal or used as a feed additive.

Certain fluid chemicals may be delivered by a suitable delivery system carried by the foregoing device. For example, a portion of the rods, shaft, or mounting rings may be covered with a layer of microporous material such as silicone rubber of the Silastic type. The fluid chemical is incorporated into the layer prior to vaginal insertion for slow long-term release thereafter.

It is apparent from the foregoing that a relatively inexpensive, non-chemical and safe method has been provided to enhance the quality and quantity of meat produced by an animal. The device is particularly effective in that it is retained in an extremely high percentage of the animals after insertion. Although the exact mechanism of the effectiveness of the device is not known, it is believed to be related to stimulation of the nerves in the vaginal wall of the animals.

What is claimed is:

1. An intra-vaginal device comprising mounting means, and a plurality of elongate resilient rods mounted at their fixed ends to radiate outwardly from said mounting means and terminating in free ends of enlarged bulbous configuration, said rods being characterized by a combination of internal memory and a configuration of changing axial direction such that when said rods are subjected to a bending moment to move said bulbous ends toward each other, said bulbous ends are urged under spring-like pressure in a radially outward direction from said mounting means, said rods being in a configuration including at least two distinct offset angle bends in a generally outward direction from said mounting means and defining an inner rod segment mounted to said mounting means, at least one middle rod segment and an outer rod segment terminating in said bulbous end, said bends providing said outward urging spring-like pressure to said bulbous ends when said rods are subjected to a bending moment toward said mounting means.

2. The device of claim 1 in which said mounting means defines a central axis and said inner rod segments project from said means at a substantial angle from said axis.

3. The device of claim 1 in which the outer rod segment is substantially shorter than the total length of said middle and inner rod segments to exert increased pressure on said bulbous end when subject to a bending moment toward said mounting means.

4. An intra-vaginal device comprising mounting means, and a plurality of elongate resilient rods mounted at their fixed ends to radiate outwardly from said mounting means and terminating in free ends of enlarged bulbous configuration, said rods being characterized by a combination of internal memory and a configuration of changing axial direction such that when said rods are subjected to a bending moment to move said bulbous ends toward each other, said bulbous ends are urged under spring-like pressure in a radially outward direction from said mounting means, said mounting means comprises at least a first mounting ring from which a plurality of said rods project and carried by an elongate shaft having a leading end and a following end, said rods being shaped to bend toward said leading end when said bulbous ends are urged toward each other.

5. The device of claim 4 in which said mounting means includes a second mounting ring also carried by said shaft axially spaced apart from said first mounting ring, another set of said elongate resilient rods projecting from said second mounting ring.

6. The device of claim 4 together with an annular cervical seating means adapted for urging against an animal's cervix, said seating means comprising an annular ring mounted to the leading end of said shaft.

7. In a method for enhancing the quality and quantity of meat produced by an animal, using a device including mounting means and a plurality of elongate resilient rods mounted at their fixed ends to radiate outwardly from said mounting means to terminate in free ends of enlarged bulbous configuration, the steps of
 (a) applying pressure to said rods to move said bulbous ends toward each other, thereby reducing the outward radial extent of the same,
 (b) inserting the device through an animal's vulva into the animal's vagina with said bulbous ends directed toward the anterior of the animal's vagina,
 (c) releasing the pressure applied in step (b) to permit said rods to expand outwardly under pressure to such an extent that said bulbous ends become embedded in the animal's vaginal lining without piercing the same to retain the device within the vagina while permitting the vulva to assume its normally closed position, and
 (d) permitting the device to remain in the vagina of the animal for a prolonged period of time.

8. The method of claim 7 in which said device is retained in the animal's vagina for sufficient time that the vaginal lining grows over said bulbous ends to form a bond therewith to assist retention of the device.

9. The method of claim 8 in which said rods become more flexible during the period of vaginal retention to cause a decrease in the outward pressure exerted by said bulbous ends during said retention period.

10. The method of claim 7 together with the step of isolating the deviced female animals.

11. The method of claim 7 including the step of releasing a fluid chemical from the device into the animal over an extended period of time.

12. An intra-vaginal device comprising mounting means, and a plurality of elongate resilient rods mounted at their fixed ends to radiate outwardly from said mounting means and terminating in free ends of enlarged bulbous configuration, said rods being characterized by a combination of internal memory and a configuration of changing axial direction such that when said rods are subjected to a bending moment to move said bulbous ends toward each other, said bulbous ends are urged under spring-like pressure in a radially outward direction from said mounting means, said rods being formed of a hygroscopic material characterized by increasing flexibility under the heat and moisture conditions in an animal's vagina compared to room temperature and relative humidity.

* * * * *